US009202661B2

(12) United States Patent
Holm et al.

(10) Patent No.: US 9,202,661 B2
(45) Date of Patent: Dec. 1, 2015

(54) ELECTRON BEAM DEVICE FOR SHAPING AN ELECTRIC FIELD AND A METHOD OF MANUFACTURING SAID ELECTRON BEAM DEVICE THE SAME

(75) Inventors: Kurt Holm, Baden (CH); Toni Waber, Aefligen (CH); Urs Hostettler, Thun (CH); Hans Vonäsch, Niederscherli (CH)

(73) Assignee: TETRA LAVAL HOLDINGS & FINANCE S.A., Pully (CH)

(*) Notice: Subject to any disclaimer, the term of this patent is extended or adjusted under 35 U.S.C. 154(b) by 0 days.

(21) Appl. No.: 14/126,179

(22) PCT Filed: Jun. 27, 2012

(86) PCT No.: PCT/EP2012/062454
§ 371 (c)(1),
(2), (4) Date: Dec. 13, 2013

(87) PCT Pub. No.: WO2013/004565
PCT Pub. Date: Jan. 10, 2013

(65) Prior Publication Data

US 2014/0117259 A1 May 1, 2014

Related U.S. Application Data

(60) Provisional application No. 61/525,136, filed on Aug. 18, 2011.

(30) Foreign Application Priority Data

Jul. 4, 2011 (SE) ...................................... 1100519

(51) Int. Cl.
*A61N 5/00* (2006.01)
*H01J 29/02* (2006.01)
(Continued)

(52) U.S. Cl.
CPC . *H01J 29/02* (2013.01); *G21K 5/04* (2013.01); *H01J 3/38* (2013.01); *H01J 9/18* (2013.01); *Y10T 29/49002* (2015.01)

(58) Field of Classification Search
CPC .............. H01J 3/02; H01J 1/94; A61L 2/007; A61L 2/087
USPC ........................................................ 250/492.3
See application file for complete search history.

(56) References Cited

U.S. PATENT DOCUMENTS

| | | | | |
|---|---|---|---|---|
| 3,144,552 | A * | 8/1964 | Schonberg et al. | 250/400 |
| 3,831,052 | A * | 8/1974 | Knechtli | 313/595 |

(Continued)

FOREIGN PATENT DOCUMENTS

| | | | |
|---|---|---|---|
| JP | 2001-021700 | A | 1/2001 |
| JP | 2005-241521 | A | 9/2005 |
| WO | WO 2010/040454 | A2 | 4/2010 |

OTHER PUBLICATIONS

International Search Report (PCT/ISA/210) mailed on Oct. 8, 2012, by the European Patent Office as the International Searching Authority for International Application No. PCT/EP2012/062454.

*Primary Examiner* — Nicole Ippolito
*Assistant Examiner* — Jason McCormack
(74) *Attorney, Agent, or Firm* — Buchanan Ingersoll & Rooney PC

(57) ABSTRACT

An electron beam device having a tubular body of elongate shape with an electron exit window extending in the longitudinal direction of the tubular body. The tubular body is at least partly forming a vacuum chamber, the vacuum chamber comprising therein a cathode comprising a cathode housing having an elongate shape, and at least one electron generating filament and a control grid both extending along the elongate shape of the cathode housing. The control grid and the cathode housing are attached to each other by attachment mechanisms. Free longitudinal end portions of either the control grid or the cathode housing are bent in a direction towards each other to form bulge-like shapes for the formation of electron beam shaping electrodes. The invention is further comprising a method of manufacturing the electron beam device.

17 Claims, 4 Drawing Sheets

(51) Int. Cl.
*G21K 5/04* (2006.01)
*H01J 3/38* (2006.01)
*H01J 9/18* (2006.01)

(56) References Cited

U.S. PATENT DOCUMENTS

| | | | | |
|---|---|---|---|---|
| 4,008,413 | A | 2/1977 | Bayless | |
| 4,376,257 | A * | 3/1983 | Miyazaki et al. | 313/417 |
| 4,376,258 | A * | 3/1983 | Glock | 313/422 |
| 4,755,722 | A * | 7/1988 | Wakalopulos | 315/111.31 |
| 6,426,507 | B1 * | 7/2002 | Rangwalla et al. | 250/492.3 |
| 6,528,799 | B1 * | 3/2003 | Katsap et al. | 250/398 |
| 2007/0290148 | A1 * | 12/2007 | Kristiansson et al. | 250/492.3 |
| 2011/0198513 | A1 | 8/2011 | Holm | |

* cited by examiner

ELECTRON BEAM DEVICE FOR SHAPING AN ELECTRIC FIELD AND A METHOD OF MANUFACTURING SAID ELECTRON BEAM DEVICE THE SAME

FIELD OF THE INVENTION

The present invention relates to an electron beam device and a method of manufacturing said electron beam device.

BACKGROUND OF THE INVENTION

A typical electron beam device comprises a hermetically sealed, i.e. vacuum tight, body inside which a cathode housing is arranged. The cathode housing comprises a filament which is heated by a current in order for electrons to be produced. The thus produced electrons are accelerated by means of a high-voltage potential and exits through an exit window of the body, typically a thin window foil supported by a support grid. Electron beam devices may be used for several purposes, such as curing of ink or adhesives, or sterilisation of volumes or surfaces. Depending on the application properties such as acceleration voltage, beam profile, shape of the electron beam device will vary. The teachings of the present invention may advantageously be applied to electron beam devices used for sterilization of a web of packaging material, since it may significantly improve the performance of electron beam devices being designed for that purpose. It is to be understood, however that it may be applied to other electron beam devices having a similar construction.

Within the field of sterilization of a web of packaging material, performance factors such as stability, durability and longevity are key issues, once the quality of the sterilization is ensured. All components mentioned and still more may be optimized in order for the electron beam device to produce the desired beam shape under any given circumstances.

The present invention relates to the context of elongate electron beam devices used for treatment of larger surface, such as webs of packaging material used for production of packaging containers. More specifically the present invention relates to improvements of such electron beam devices, in terms of ensuring adequate quality while simplifying assembly of the electron beam device.

SUMMARY OF THE INVENTION

The present invention relates to an electron beam device having a tubular body of elongate shape with an electron exit window extending in the longitudinal direction of the tubular body, said tubular body at least partly forming a vacuum chamber, said vacuum chamber comprising therein a cathode comprising a cathode housing having an elongate shape, and at least one electron generating filament and a control grid both extending along the elongate shape of the cathode housing. The control grid and the cathode housing are attached to each other by attachments means, and free longitudinal end portions of either the control grid or the cathode housing are bent in a direction towards each other to form bulge-like shapes for the formation of electron beam shaping electrodes. In this way an electron beam device is provided which has a cathode being easy to manufacture and assemble, and which is being able to shape the electric field in such a way that the electrons hit the electron exit window in a direction essentially perpendicular to the plane of the exit window. With the inventive electron beam device an electron beam is formed being highly suitable for sterilizing for example a wide web of packaging material.

In an embodiment said control grid has an essentially centrally positioned perforated surface through which the electrons can pass, and said longitudinal end portions of either the control grid or the cathode housing are bent in a direction towards each other and in over the control grid so that the bulge-like shapes extend to longitudinal boundaries of said perforated surface. The bulge-like shape will help shaping the electric field so that the electrons will hit the exit window in an essentially right angle, i.e. in a direction essentially perpendicular to the plane of the exit window. In fact, the electrodes will make the electron trajectories "bend" slightly to the centre of the electron beam, to counteract the "bending" of the electron trajectories near the exit window where they tend to spread, i.e. the electron beam will normally be wider near the exit window than near the control grid.

In an embodiment said bulge-like shapes are formed so that its free edges are pointing in a direction essentially perpendicular to the perforated surface of the control grid. Said free edges extend essentially all the way down to the control grid. This further adds to the electron directing effect described above.

In an embodiment said longitudinal end portions, being bent to form the bulge-like shapes, are bent over the attachment means to at least partly encapsulate them. Hence, the shape of the attachment means will not have any or very little impact on the electric field, and can therefore be designed in the best way possible for attaching the cathode housing and the control grid.

In order to uniformly direct the electrons towards the control grid, the cathode housing is preferably formed as an elongate semi-annular shell, the open side of which is covered by the control grid.

In one or more presently preferred embodiments, the at least one filament is extending essentially centrally within and along said elongate semi-annular shell. This gives a compact and easy-to-assemble cathode.

In an embodiment the bulge-like shapes are formed in the control grid, wherein free longitudinal end portions of the cathode housing are bent inwards and form radial projections directed essentially parallel with the perforated surface of the control grid, wherein said attachment means are attached to said projections of the cathode housing, and wherein the attachment means are also attached to an area of the control grid, said area being provided in between the perforated surface and the bulge-like shape. This makes the parts of the cathode easy to manufacture and assemble.

In an embodiment said control grid and said cathode housing are connected to separate power supplies, and said attachment means are electrical isolator elements. This will form an electron beam device of a triode type, in which the control grid actively shapes the electron beam.

In an embodiment the electron beam device is of a triode type, in which the filament is connected to a first power supply, the cathode housing is connected to a second power supply and the control grid is connected to a third power supply, and in which the tubular body and the electron exit window are connected to ground. This is an example of an efficient triode type electron beam device.

Further embodiments are defined by the additional dependent claims.

Furthermore, the invention also provides for a method of manufacturing an electron beam device having a tubular body of elongate shape with an electron exit window extending in the longitudinal direction of the tubular body, said tubular body at least partly forming a vacuum chamber, said vacuum chamber comprising therein a cathode comprising a cathode housing having an elongate shape, and at least one electron generating filament and a control grid both extending along the elongate shape of the cathode housing. The method comprises the steps of attaching the control grid and the cathode housing to each other by attachments means, and bending free longitudinal end portions of either the control grid or the cathode housing in a direction towards each other to form bulge-like shapes for the formation of electron beam shaping electrodes.

BRIEF DESCRIPTION OF THE DRAWINGS

In the following, a presently preferred embodiment of the invention will be described in greater detail, with reference to the enclosed schematic drawings, in which.

DETAILED DESCRIPTION OF A PREFERRED EMBODIMENT

Figure 1:
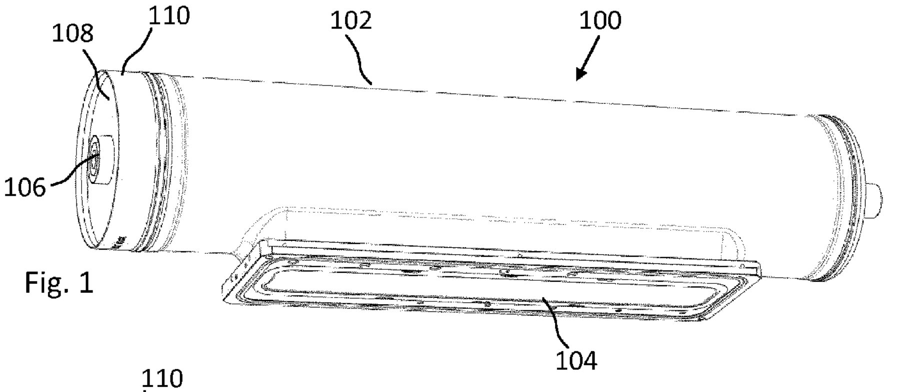
FIG. 1 is a perspective view of an electron-beam device according to one embodiment of the present invention.

FIG. 1 is a perspective view of an exemplary hermetically sealed electron beam device 100 of the present invention, showing only the exterior thereof. The purpose of the drawing is simply to illustrate the basic components of an electron beam device, and it should be emphasized that the purpose is not to provide a true constructional drawing or in any other way limit the present invention.

The main component of the electron beam device is the tubular body 102, which has an elongate shape. An exit window arrangement 104 provides an outlet for electrons from the vacuum inside the tubular body 102. The exit window arrangement 104 in turn comprises subassemblies not relevant for the present invention, yet having the properties of providing an outlet window for electrons while preserving vacuum inside the body 102. A proximal end of the body 102 comprises an assembly including electrical connections 106, and an insulating ceramic disc 108 sealing towards the assembly and an inner perimeter of the body 102. In the present embodiment the ceramic disc 108 actually seals towards the inner perimeter of a cylindrical component 110 which in turn is welded to the elongate body. For reasons not relevant for the present invention this arrangement simplifies assembly, disassembly, and reassembly of the electron beam device.

Inside the tubular body 102 a cathode is arranged. The cathode comprises a cathode housing 112, which is one of the components illustrated in FIGS. 2 and 3. The cylindrical component 110 and the ceramic disc 108 are clearly visible, and the skilled person realizes how the illustrated arrangement may be inserted in the tubular body 102 for forming the assembly of FIG. 1. The cathode housing 112 is formed as a semi-annular shell, the open side of which is covered by a control grid 114. Inside the annular shell of the cathode housing 112 one or more filaments 120 (see FIG. 3) are arranged, extending from a proximal end of the cathode housing 112 to a distal end thereof. In use, an electron beam is generated by heating the filament 120, using a current, and by accelerating the electron towards the exit window 104 by means of a high-voltage potential between the cathode housing 112 and the exit window 104 (being the anode). The high-voltage potential is created by for example connecting the cathode housing to a power supply and by connecting the tubular body to ground.

By applying an electrical potential also to the control grid 114 the emission of electrons may be further controlled. If a separate and variable electrical potential is applied to the control grid 114 it makes it possible to use the control grid 114 for active shaping of the generated electron beam. For these purposes the control grid 114 may be electrically connected to a separate power supply (not shown). Such type of electron beam device is generally referred to as a triode. A triode is normally characterized in that the filament is connected to a first power supply, the cathode housing is connected to a second power supply and the control grid is connected to a third power supply.

The control grid 114 comprises a flat perforated surface 115 comprising a pattern of openings or through-holes for passage of electrons. The open side of the cathode housing 112, carrying the control grid 114, should for obvious reasons be facing the exit window arrangement 104.

Figure 4:
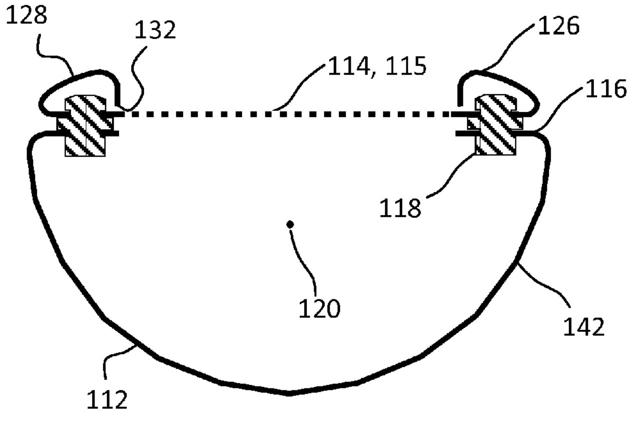
FIG. 4 is a schematic cross section of a first embodiment of the cathode of FIG. 2.

A first embodiment of the cathode is shown in FIG. 4. The free longitudinal end portions of the cathode housing 112 are bent inwards, in a direction towards each other, i.e. in a lateral direction being perpendicular to the extension of the longitudinal edges. Thereby, the edges form radial projections 116. These radial projections 116 are preferably straight and parallel with the flat perforated surface 115 of the control grid 14. The control grid 114 is attached to the said projections 116 in attachment points by means of attachment means 118. If there is a difference in electrical potential between the cathode housing 112 and the grid 114 said attachment means 118 are preferably electrical isolator elements. In that case they are preferably made of a ceramic material, for example $Al_2O_3$.

Figure 5A:
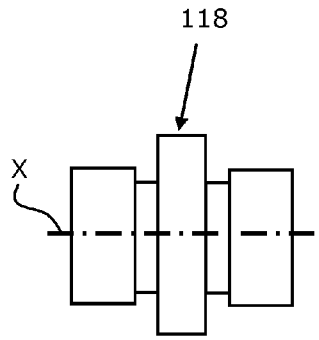
FIG. 5*a* is a view of an attachment means for attaching the control grid to the cathode housing.
Figure 5B:
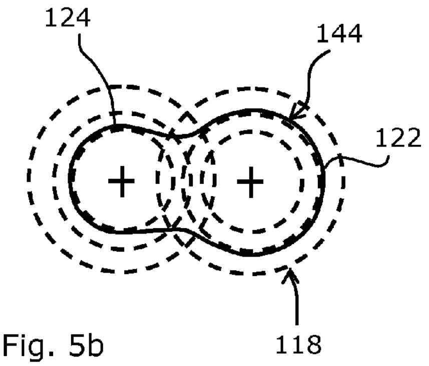
FIG. 5*b* is a view of a hole used in the control grid and the cathode housing for attaching the attachment means, the dashed line showing the largest diameter of the attachment means in two states; a mounting state and a locking state.
Figure 6B:
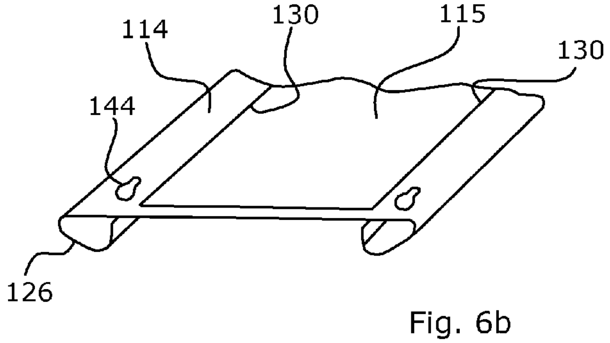
FIG. 6*b* is a perspective view of a portion of the control grid.
Figure 6A:
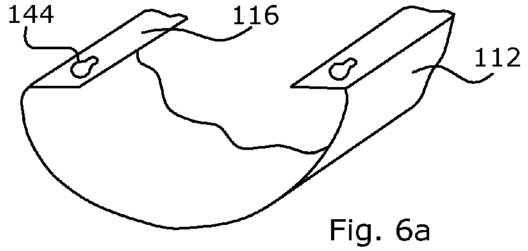
FIG. 6*a* is a perspective view of a portion of the cathode housing.

An example of an attachment means 118 is shown in FIG. 5*a*. The attachment means 118 is rotational symmetric around axis X. It comprises three portions with larger diameters and two intermediate portions of smaller diameter. The middle one of the larger diameters is larger than the others. The control grid and the cathode housing are connected to each other by the attachment means 118 via holes. A typical hole configuration 144 is shown in FIG. 5*b*. It should be pointed out that FIG. 5*a* and FIG. 5*b* are not mutually according to scale. The hole 144 comprises a circular portion 122 with a larger diameter and an oblong-shaped portion 124 with a smaller diameter. The larger diameter of the circular portion 122 is slightly larger than the second largest diameter of the attachment means 118. The smaller diameter of the oblong-shaped portion 124 is slightly smaller than or essentially equal to the smaller, intermediate, diameter of the attachment means 118. In FIG. 6*a* a portion of the cathode housing 112 is shown with the radial projections 116 clearly visible. The radial projections 116 are provided with through-going holes of the described hole configuration 144 of FIG. 5*b*. Several such holes 144 are provided along the longitudinal extension of the radial projection 116. Similarly, several such holes 144 are provided in the control grid 114. The holes 144 are arranged in an area being provided in between the perforated surface 115 and a bulge-like shape 126, the latter being described further down. It is to be noted that FIG. 6*b* shows the control grid "upside down", meaning that the perforated surface 115 adapted to face the cathode housing is clearly visible in this view. Further, for simplicity, the perforated surface 115 is here shown blank (the pattern of through-going openings for the electrons are non-visible).

The arrangement means 118 is mounted in the hole 144 by putting of its ends through the larger circular portion 122 of the hole 144. A radial surface of the largest diameter of the attachments means 118 will then rest on the surface around the hole 144 in the projection 116. The attachment means 118 is thereby in a mounting state. Then, the attachment means 118 is slid towards the smaller oblong-shaped portion 124 of the hole 144 where it is held firmly. This is the locking state. The position of the attachments means 118 in the mounting state and the locking state are shown as dashed lines in FIG. 5*b*. The control grid 114 and the cathode housing 112 are mounted to each other by arranging one attachments means 118 in each hole 144 of the cathode housing 120 and sliding the attachments means 118 to the locking state. The control grid 114 is then arranged so that the attachments means 118 mounted to the cathode housing 112 are, in their other ends, received in the larger circular portions of the holes 144 of the control grid 114. The control grid 114 is then slid in place on top of the cathode housing 112, meaning that the control grid 114 is displaced so that the attachment means 118 end up in the smaller oblong-shaped portions 124 of the holes 144 in the control grid 114.

In the first embodiment of the cathode, shown in FIG. 4, free longitudinal end portions 128 of the control grid 114 are bent in a direction towards each other, i.e. in a lateral direction being perpendicular to the extension of the longitudinal end portions, to form bulge-like shapes 126 for the formation of electron beam shaping electrodes. Such electrodes are sometimes referred to as "Wehnelt" electrodes. The bulge-like shape will assist in the generation of a smooth predictable electrical field to the benefit of performance of the electron beam device 100. They help shaping the electric field so that the electrons will hit the exit window 104 in an essentially right angle, i.e. in a direction essentially perpendicular to the plane of the exit window 104. In fact, the electrodes will make the electron trajectories "bend" slightly to the centre of the electron beam, to counteract the "bending" of the electron trajectories near the exit window 104 where they tend to spread, i.e. the electron beam will normally be wider near the exit window 104 than near the control grid 114.

The wording "bulge-like shape" should not be interpreted in a limited way, but should here be interpreted as any shape forming for example a bulge, a bead, a curl, a curve, a wave or a half-circle. It can also mean a more linear shape such as a shape made up by a polygonal chain, for example a half rectangular shape.

The control grid 114 is bent in a way so that it is curled over itself, towards its centrally positioned perforated surface 115. The bulge-like shapes 126 are made to extend to longitudinal boundaries 130 of the perforated surface 115. Further, the bulge-like shapes 126 are formed so that its free edges 132 are pointing in a direction essentially perpendicular to the perforated surface 115 of the control grid 114. Said free edges 132 extend essentially all the way down to the control grid 114 leaving only a small gap. As can be seen in FIG. 4 the longitudinal end portions 128 are being bent over the attachment means 118 to at least partly encapsulate them.

Figure 2:
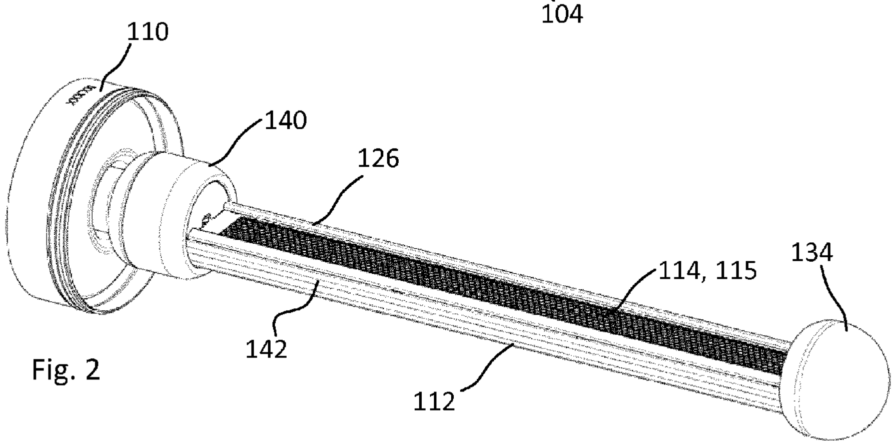
FIG. 2 is a perspective view of a cathode which may be used in the electron-beam device of FIG. 1.

The described cathode is fitted into the electron beam device as shown in FIG. 2. The proximal end as well as the distal end of the cathode housing 112 comprises electrical connections as well as physical suspensions for the filament 120. At the distal end this arrangement is housed inside or covered with a dome-shaped cap 134. The application of the dome-shaped cap will in an effective manner shield the components inside the cap from the electrical field outside the cap, and vice versa, e.g. implying that the shape of the components inside the cap will not be able to affect the electrical field in a detrimental way.

Figure 3:
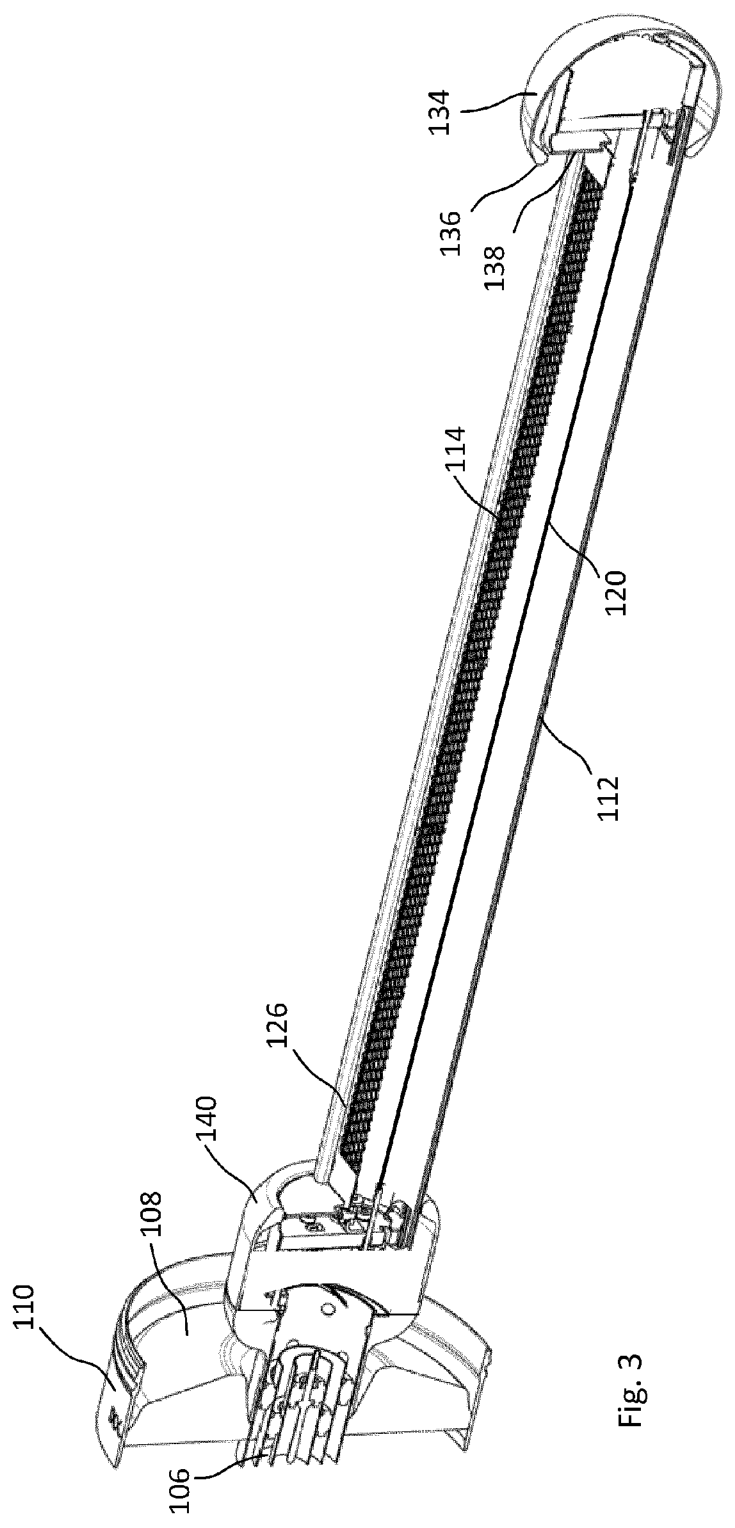
FIG. 3 is a longitudinal section of the cathode of FIG. 2.

The cap 134 has the form of a spherical shell with part of the shell cutaway such that it comprises slightly more than a semi-sphere, which is illustrated in FIG. 3. The cap 134 of the present embodiment is axisymmetric and the free end is provided with a solid bulge 136, which gives the free edge a smooth appearance too, meaning that the field strength may be kept low. The opening of the cap 134, as defined by the inner perimeter of the bulge 136 is dimensioned to fit over the semi-annular shell of the cathode housing 112, such that a portion of the housing may be inserted therein. The opening of the cap 136 has the same diameter as the curvature of the semi-annular shell, effectively closing a lower half of the opening. The upper half of the opening may be covered by a plate 138, preventive the electrical field from entering the cap 134, and positioning the cathode housing 112 in relation to the cap 134. The cap 134 may be said to comprise an open end (where the free edge and the bead are situated) and a semi-sphere, formed in one piece.

At its proximal end the cathode housing 112 is suspended to the elongate body. This suspension may be provided in more than one way, and the suspension best seen in FIG. 3 is one option not previously shown. The cathode housing is effectively suspended in a central opening of the disc 108, with some intermediate components not discussed in detail in the present specification. To avoid distortion of the electrical field in the proximal end it is provided with a cap too, which will be referred to as 'the proximal cap' 140 in the following. The free edge at the open end of the proximal cap 140 is provided with a bead, and the open end as such is essentially identical to the corresponding end of the cap 134. However, while the cap 134 was said to comprise the open end and a semi-sphere, the proximal cap 140 comprises the open end and a cylindrical shell, such that it may fit over and to the suspension arrangement at the proximal end of the tube body.

Preferably, the cathode housing, the tubular body and the control grid are all made of stainless steel.

In FIGS. 2 and 4 it is apparent that the cross section of the semi-annular shell of the cathode housing 112 is not smoothly rounded, but is formed with facets 142 or as a polygonal chain. This considerably facilitates the bending process used during manufacture of the electron beam device. Further, the cathode housing 112 is provided with a number of strut sections (not shown) functioning as stiffeners cross the elongate shape of the cathode housing 112.

Figure 7:
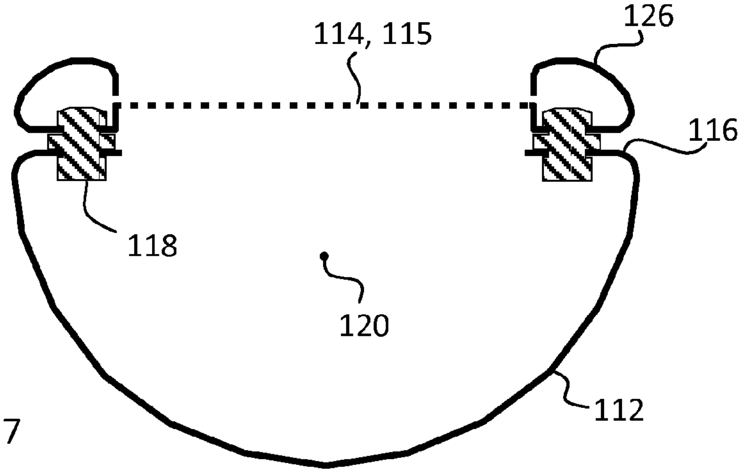
FIG. 7 is a schematic cross section of a second embodiment of the cathode.

A second embodiment of the cathode is shown in FIG. 7. For easiness the same reference numbers will be used for corresponding elements and only the differences between the first and second embodiments will be described. As can be seen in the figure, the second embodiment is very similar to the first one. It is basically only the control grid 114 and its bulge-like shapes 126 that have a different shape. The control grid 114 is bent so that the plane of the perforated surface 115 is displaced from the plane constituting the area in which the holes 120 for the attachment means 118 are provided. The perforated surface 115 is displaced in a direction away from the cathode housing 112. This embodiment has a more complex design than the first one, but has a lower field strength.

Figure 8:
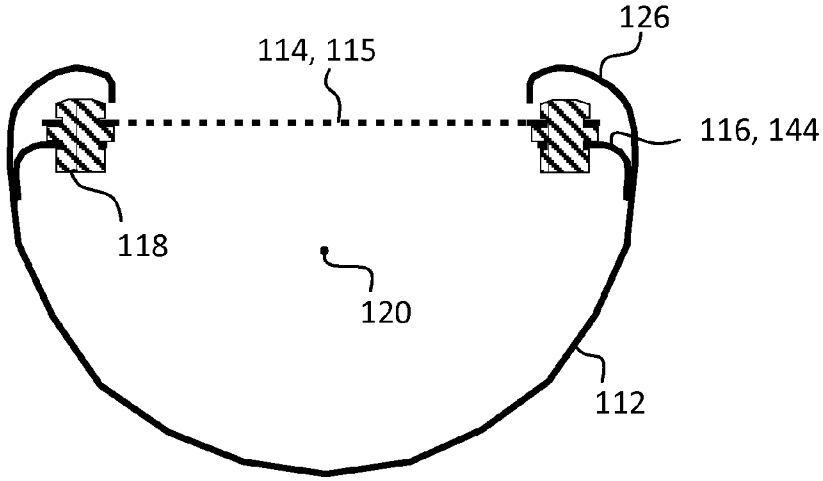
FIG. 8 is a schematic cross section of a third embodiment of the cathode.

A third embodiment of the cathode is shown in FIG. 8. For easiness the same reference numbers will be used also here for corresponding elements and only the differences between the first and third embodiments will be described. In this third embodiment it is the free longitudinal end portions of the cathode housing 112 that are bent in a direction towards each other to form the bulge-like shapes 126 for the formation of electron beam shaping electrodes. Radial projections 116 adapted for holding the attachments means 118 are formed by elements 144 attached to the inner surface of the cathode housing 112. The elements 144 may preferably be welded or brazed to the surface. Other alternative attachment methods are for example gluing, riveting or screwing. By means of the elements 144 the control grid 114 can be held in a position similar to that of the first embodiment.

The invention further comprises a method of manufacturing an electron beam device 100 having a tubular body 102 of elongate shape with an electron exit window 104 extending in the longitudinal direction of the tubular body 102. The tubular body 102 is at least partly forming a vacuum chamber. Said vacuum chamber is comprising therein a cathode comprising a cathode housing 112 having an elongate shape, and at least one electron generating filament 120 and a control grid 114 both extending along the elongate shape of the cathode housing 112. The method comprises the steps of attaching the control grid 114 and the cathode housing 112 to each other by attachments means 118, and bending free longitudinal end portions 122 of either the control grid 114 or the cathode housing 112 in a direction towards each other to form bulge-like shapes for the formation of electron beam shaping electrodes.

Although the present invention has been described with respect to a presently preferred embodiment, it is to be understood that various modifications and changes may be made without departing from the object and scope of the invention as defined in the appended claims.

The invention claimed is:

1. An electron beam device having a tubular body of elongate shape with an electron exit window extending in the longitudinal direction of the tubular body, said tubular body at least partly forming a vacuum chamber, said vacuum chamber comprising therein a cathode comprising a cathode housing having an elongate shape, and at least one electron generating filament and a control grid both extending along the elongate shape of the cathode housing wherein the control grid and the cathode housing are attached to each other wherein longitudinal end portions of either the control grid or the cathode housing are bent in a direction towards each other to form bulge-like shapes for the formation of electron beam shaping electrodes, and wherein free edges of the longitudinal end portions of either the control grid or the cathode housing face an outside surface of the control grid.

2. The electron beam device according to claim 1, wherein said control grid has an essentially centrally positioned perforated surface through which the electrons can pass, and wherein said longitudinal end portions of either the control grid or the cathode housing are bent in a direction towards each other and in over the control grid so that the bulge-like shapes extend to longitudinal boundaries of said perforated surface.

3. The electron beam device according to claim 1, said bulge-like shapes are formed so that its free edges are pointing in a direction essentially perpendicular to the perforated surface of the control grid.

4. The electron beam device according to claim 3, said free edges extend essentially all the way down to the control grid.

5. The electron beam device according to claim 1, wherein said longitudinal end portions, being bent to form the bulge-like shapes, are bent over the attachment means to at least partly encapsulate them.

6. The electron beam device according to claim 1, wherein the cathode housing is formed as an elongate semi-annular shell, the open side of which is covered by the control grid.

7. The electron beam device according to claim 6, wherein the at least one filament is extending essentially centrally within and along said elongate semi-annular shell of the cathode housing.

8. The electron beam device according to claim 2, wherein the bulge-like shapes are formed in the control grid, wherein free longitudinal end portions of the cathode housing are bent inwards and form radial projections directed essentially parallel with the perforated surface of the control grid, wherein said attachment means are attached to said radial projections of the cathode housing, and wherein the attachment means are also attached to an area of the control grid, said area being provided in between the perforated surface and the bulge-like shape.

9. The electron beam device according to claim 1, wherein said control grid and said cathode housing are connected to separate power supplies, and wherein said attachment means are electrical isolator elements.

10. The electron beam device according to claim 9, wherein the electron beam device is of a triode type, in which the filament is connected to a first power supply, the cathode housing is connected to a second power supply and the control grid is connected to a third power supply, and in which the tubular body and the electron exit window are connected to ground.

11. The electron beam device according to claim 1, wherein the cathode housing is made of stainless steel.

12. The electron beam device according to claim 1, wherein the control grid is made of stainless steel.

13. The electron beam device according to claim 1, wherein the tubular body is made of stainless steel.

14. The electron beam device according to claim 1, wherein the attachments means are made of ceramic material.

15. Method of manufacturing an electron beam device having a tubular body of elongate shape with an electron exit window extending in the longitudinal direction of the tubular body, said tubular body at least partly forming a vacuum chamber, said vacuum chamber comprising therein a cathode comprising a cathode housing having an elongate shape, and at least one electron generating filament and a control grid both extending along the elongate shape of the cathode housing, wherein the method comprises attaching the control grid and the cathode housing to each other, and bending longitudinal end portions of either the control grid or the cathode housing in a direction towards each other to form bulge-like shapes for the formation of electron beam shaping electrodes, wherein free edges of the longitudinal end potions of either the control grid or the cathode housing face an outside surface of the control grid.

16. An electron beam device comprising: an elongated tubular body with an electron exit window extending in the longitudinal direction of the tubular body, the tubular body at least partly forming a vacuum chamber in which is located a cathode comprising a cathode housing having an elongate shape, and at least one electron generating filament and a control grid both extending along the elongate shape of the cathode housing, the control grid and the cathode housing being attached to each other, the control grid including a perforated surface permitting the electrons to pass through the control grid, the control grid including longitudinally extending free end portions that are bent towards each other to form bulge-shape electron beam shaping electrodes, the control grid and the cathode housing being attached to each other by electrical isolator elements arranged between the perforated surface and the bilge-shape electron beam shaping electrode, and wherein the bulge-shape electron beam shaping electrodes are bent over the electrical isolator elements to at least partly encapsulate the electrical isolator elements, and the bulge-shape electron beam shaping electrodes possessing free edges facing and outside surface of the control grid.

17. The electron beam device according to claim 16, wherein the cathode housing is an elongate semi-annular shell possessing an open side covered by the control grid.

* * * * *